United States Patent [19]
Hofheinz et al.

[11] Patent Number: 4,977,184

[45] Date of Patent: Dec. 11, 1990

[54] BICYCLIC PEROXIDES COMPOSITIONS FOR AND TREATMENT OF MALARIA THEREWITH

[75] Inventors: Werner Hofheinz, Bottmingen; Gérard Schmid, Kienberg; Harro Stohler, Binningen, all of Switzerland

[73] Assignee: Hoffmann-La Roche Inc., Nutley, N.J.

[21] Appl. No.: 250,666

[22] Filed: Sep. 29, 1988

[30] Foreign Application Priority Data

Oct. 15, 1987 [CH] Switzerland ............... 4032/87
Jul. 8, 1988 [CH] Switzerland ............... 2612/88

[51] Int. Cl.$^5$ ............... C07D 319/00; A61K 31/335
[52] U.S. Cl. ............... 514/452; 549/363; 546/174
[58] Field of Search ............... 514/452; 549/363

[56] References Cited

U.S. PATENT DOCUMENTS 3,900,500 9/1975 Woodward ............... 549/363

FOREIGN PATENT DOCUMENTS 0285342 10/1988 European Pat. Off. ............ 549/363

OTHER PUBLICATIONS

Acta Chim. Sinica 37, 215–230 (1979).
Chia-Chiang Shen, Medical Research Review, 4, 47, 48, 51–59, & 82–86.
Liang Advances in Chinese Medical Materials Research, Chang et al. Eds., World Scientific Publ. Co., Singapore, 1985: pp. 427–432.
Abstracts and Posters, XII International Congress for Topical Medicine and Malaria, Dept., 1985 Amsterdam.

*Primary Examiner*—David B. Springer
*Attorney, Agent, or Firm*—George M. Gould; Bernard S. Leon; William H. Epstein

[57] ABSTRACT

Novel 4-substituted-4,8-dimethyl-2,3-dioxabicyclo[3.3.1] nonan-7-ones which have a pronounced activity against the causative organism of malaria and can be used for the prevention and control of malaria.

61 Claims, No Drawings

BICYCLIC PEROXIDES COMPOSITIONS FOR AND TREATMENT OF MALARIA THEREWITH

SUMMARY OF THE INVENTION

The present invention is directed for bicyclic peroxides of the formula

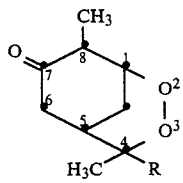

I wherein R is a saturated or unsaturated hydrocarbon group with from 1 to 15 carbon atoms or an aryl, heteroaryl, arylcarbonyl or heteroarylcarbonyl group attached via an alkyl or alkenyl group with from 1 to 7 carbon atoms.

The novel compounds of formula I above possess valuable pharmacological properties. In particular, they exhibit a pronounced activity against the causative organism of malaria and can be used for the prevention and control of malaria i.e. for prophylaxis and therapy of malaria.

Objects of the present invention are: the above compounds of formula I per se and their use as therapeutically active substances; process and intermediates for their manufacture, medicaments based on these novel substances; as well as the use of the novel compounds of formula I for the prevention and control of malaria and for the manufacture of medicaments which are suitable for the prevention and control of malaria.

DETAILED DESCRIPTION

The term "lower" used below denotes residues and compounds with a maximum of 7, preferably a maximum of 4, carbon atoms. The term "alkyl" taken alone or in combinations such as "alkyl group" and "alkoxy" denotes monovalent aliphatic straight-chain or branched, saturated hydrocarbons such as methyl, ethyl, n-propyl, i-propyl, n-butyl, s-butyl, i-butyl, i-pentyl, n-pentyl, n-hexyl, n-heptyl, n-octyl, n-nonyl, n-decyl, n-undecyl, n-dodecyl, n-tridecyl, n-tetradecyl and n-pentadecyl. The term "alkenyl" denotes straight-chain or branched monovalent aliphatic hydrocarbons which contain at least two carbon atoms and at least one olefinic double bond such as vinyl, allyl, 1-propenyl, 1-butenyl, 1-pentenyl, 1-hexenyl, 1-heptenyl, 1-octenyl, 1-nonenyl, 1-decenyl, 1-undecenyl, 1-dodecenyl, 1-tetradecenyl and 4,8-dimethyl-1,3,7-nonatrienyl.

The term "saturated or unsaturated hydrocarbon qroup" designates open chain aliphatic hydrocarbons and cycloaliphatic hydrocarbons as well as combinations thereof where the hydrocarbon group contains from 1 to 15 carbon atoms. Among the preferred open chain aliphatic hydrocarbons are alkyl containing from 1 to 13 carbon atoms and alkenyl groups of from 2 to 15 carbon atoms containing at least one double bond and preferably from 1 to 4 double bonds. Examples of alkyl and alkenyl groups are those defined above. The cycloaliphatic groups are cycloalkyl or cycloalkenyl groups containing from 3 to 10 carbon atoms and include mono-, bi- and tricycloalkyl groups. The cycloalkenyl groups contain at least one unsaturated bond and preferably from 1 to 3 unsaturated double bonds. The preferred cycloalkyl groups are cyclopropyl, cyclohexyl, cyclopentyl and adamantyl. The cycloalkyl or cycloalkenyl group can be attached via an alkenyl or alkyl group to form the saturated or unsaturated hydrocarbon substituent such as 3-(1-adamantyl)propenyl, cyclopropyl-methyl and 2-cyclohexylethyl. The cycloalkyl and cycloalkenyl moieties contain form 3 to 10 carbon atoms.

The term "aryl" denotes carbocyclic aromatic groups, containing 6 to 12 carbon atoms, preferably mono- or bicyclic groups, i.e. phenyl and naphthyl groups, especially phenyl groups. Preferably, these groups are unsubstituted or substituted with from 1 to 5 substituents selected from lower alkyl, lower alkoxy, halogen, trifluoromethyl, phenyl and cyano, whereby the substituents can be the same or different. They are preferably mono-, di- or penta-substituted by halogen, especially fluorine or chlorine, and/or trifluoromethyl. As examples of such groups there are to be mentioned: phenyl, 4-fluorophenyl, pentafluorophenyl, 4-cyanophenyl, 2-chloro-4-cyanophenyl, 3,5-dicyanophenyl, 2-chloro-4-(trifluoromethyl)phenyl, 4-methoxyphenyl, 4-methylphenyl, 4-(t-butyl)phenyl, 4-chlorophenyl 2,4-dichlorophenyl, 3,4-dichlorophenyl, 3-(trifluoromethyl)phenyl, 4-(trifluoromethyl)phenyl, 3,5- and 2,4-bis(trifluoromethyl)phenyl, 4-biphenyl, 1-naphthyl and 4-bromo-1-naphthyl.

The term "heteroaryl" denotes heterocyclic aromatic rings. Preferably mono- or bicyclic rings with 5 to 12 members in the ring. In the case of the bicyclic groups one of the aromatic rings is preferably carbocyclic. The preferable hetero atom is nitrogen with rings which contain 1, 2 or 3 nitrogen atoms as the only hetero atom being especially preferred. Preferred groups are pyridyl, pyrimidyl and especially quinolinyl groups. Preferably, these groups are unsubstituted or substituted with from 1 to 5 substituents selected from lower alkyl, lower alkoxy, halogen, trifluoromethyl, phenyl and cyano, whereby the substituents can be the same or different. They are preferably substituted, particularly mono-, di- or trisubstituted by halogen, especially chlorine or fluorine, and/or trifluoromethyl. Examples of such groups are: 2,7-bis(trifluoromethyl)-4-quinolinyl, 2,8-bis(trifluoromethyl)-4-quinolinyl and 6,8-dichloro,2-(trifluoromethyl)-4-quinolinyl.

The term "halogen" denotes the four forms i.e. fluorine, chlorine, bromine and iodine.

Insofar as R has a significance different from methyl, the compounds of formula I have four asymmetrically substituted carbon atoms. Where R signifies methyl, the corresponding compounds of formula I have three asymmetrically substituted carbon atoms. The present invention embraces all possible stereoisomers, especially the (1R,4R,5S,8R)-, (1R,4S,5S,8R)-, (1S,4R,5R,8S)- and the (1S,4S,5R,8S)-isomers and mixtures thereof.

In accordance with an embodiment of this invention, there are provided compounds of the formula

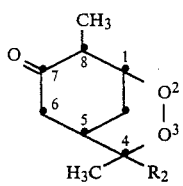

I-B wherein R₂ is alkyl containing from 1 to 15 carbon atoms, alkenyl containing from 2 to 15 carbon atoms, cycloalkyl containing from 4 to 15 carbon atoms. cycloalkenyl containing from 4 to 15 carbon atoms, cycloalkylloweralkenyl, cycloalkylloweralkyl, cycloalkenylloweralkyl, cycloalkenylloweralkenyl, aryl containing 6 to 12 carbon atoms, arylloweralkyl, arylcarbonyl containing from 7 to 13 carbon atoms. arylloweralkenyl, arylcarbonylower alkyl, arylcarbonylloweralkenyl, or a heteroaryl containing substituent selected from the group consisting of heteroaryl, heteroarylcarbonyl, heteroarylloweralkyl heteroalkylloweralkenyl, heteroarylcarbonyl lower alkyl and heteroarylcarbonylloweralkenyl where the heteroaryl moiety in said heteroaryl substituent contains a mono or bicyclic ring structure with from 5 to 12 members in said ring structure and from 1 to 3 nitrogen atoms as the only hetero atom in said ring structure with each ring in said ring structure containing from 5 to 6 ring members.

In a special embodiment the present invention is concerned with compounds of formula I where R is a saturated, preferably open-chain and straight-chain, hydrocarbon group with 8-12 carbon atoms.

In the scope of this aspect the compounds listed hereinafter are especially preferred:

4,8-Dimethyl-4-octyl-2,3-dioxabicyclo[3,3,1]nonan-7-one, 4,8-dimethyl-4-nonyl-2,3-dioxabicyclo[3,3,1]nonan-7-one 4-deoyl-4,8-dimethyl-2 3-dioxabicyclo[S,3,1]nonan,7-one, 4 8-dimethyl-4-undecyl-2 3-dioxabicyclo[3,3,1]nonan-7-one and 4-dodecyl-4 8-dimethyl-2 3-dioxabicyclo[3,3,1]nonan-7-one.

In another embodiment of the present invention, are compounds of formula I where R is an aryl or heteroaryl group attached via lower alkenyl group, i.e., an alkenyl group containing from 2 to 7 carbon atoms. The aryl group in this case is preferably a phenyl group which can be unsubstituted or mono, di or pentasubstituted with halogen, especially fluorine or chlorine, and/or trifluoromethyl and the heteroaryl group is preferably a quinolinyl group which is unsubstituted or mono-, di- or trisubstituted with halogen, especially chlorine or fluorine, and/or trifluoromethyl.

In the scope of this aspect the compounds listed hereinafter are especially preferred:

4-[(Z)-2-[2,7-bis(trifluoromethyl)-4-quinolinyl]-vinyl]4,8-dimethyl-2,3-dioxabicyclo[3,3,1]nonan-7-one, 4-[(Z)-2,4-dichlorostyryl]-4,8-dimethyl-2,3-dioxabicyclo[3,3,1]nonan-7-one.

4-[(Z)-2,4-bis(trifluoromethyl)styryl-4,8-dimethyl-2,3-dioxabicyclo[3,3,1]nonan,7-one and 4,8-dimethyl-4-[(E)-2,3,4,5,6-Pentafluorostyryl]-2,3-dioxabicyclo[3,3,1]nonan-7-one.

The novel compounds of formula I can be manufactured in accordance with the invention by (a) cyclizing a compound of the general formula

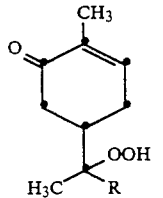

wherein R has the above significance, in the presence of a base or of an acid, or (b) reacting a compound of the formula

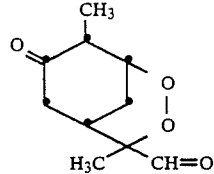

with a phosphorane of the general formula

wherein φ signifies phenyl and R' signifies hydrogen, a saturated or partially unsaturated hydrocarbon group with up to 13 carbon atoms or an heteroaryl, arylcarbonyl or heteroarylcarbonyl group attached via an alkyl or alkenyl group with up to 5 carbon atoms, or (c) reducing the double bond in a compound of the general formula

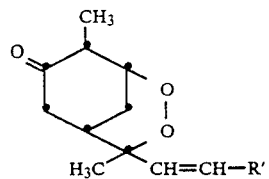

wherein R' has the above significance.

In accordance with process variant a) the compounds of formula I can be manufactured by cyclizing a hydroperoxide of general formula II in the presence of a base or of an acid. This cyclization is preferably carried out in an organic solvent, with e.g. lower alcohols such as methanol and ethanol, open-chain and cyclic ethers such as diethyl ether, t-butyl methyl ether and tetrahydrofuran, halogenated hydrocarbons such as methylene chloride and chloroform, dimethylacetamide, dimethylformamide, acetone and acetonitrile coming into consideration for this purpose. As the solvent there are preferably used lower alcohols, especially methanol, or acetonitrile. Suitable bases are the tertiary amines such as triethylamine and the lower alkali metal alcoholates such as sodium methylate, with the latter being preferred. Suitable acids are mineral acids such as hydrochloric acid, sulphuric acid and phosphoric acid, orqanic sulphonic acids for example lower alkylsulphonic acids such as methanesulphonic acid and aromatic sulphonic acids such as benzenesulphonic acid, mesitylenesulphonic acid and p-toluenesulphonic acid, and Lewis acids such as boron trifluoride. p-Toluenesulphonic acid is preferably used as the acid. The cyclization is preferably carried out in a temperature range from about 0° to about 40° C.

In a preferred embodiment p-toluenesulphonic acid in acetonitrile is used and the cyclization is carried out at room temperature.

Mixtures of stereoisomers, especially of epimers with respect to the 4-position, obtained in the cyclization can be separated by chromatographic methods or by crystallization.

Compounds of formula I in which R signifies the group —CH=CH—R' and R' has the above significance can be manufactured by reacting an aldehyde of formula III with a phosphorane of formula IV in accordance with process variant (b). Stable phosphoranes can be reacted directly with an aldehyde of formula III, with any inert organic solvent coming into consideration as the solvent. There are preferably used openchain and cyclic ethers such as diethyl ether, t-butyl methyl ether and tetrahydrofuran or halogenated lower hydrocarbons such as methylene chloride and chloroform. The remaining phosphoranes must be prepared previously in situ from the corresponding phosphonium salts and a strong base. As the base there can be used, for example, a lower alkyllithium such as n-butyllithium, sodium hydride or sodium bis-trimethylsilylamide. As solvents there especially come into consideration in this case open-chain or cyclic ethers such as diethyl ether, t-butyl methyl ether and tetrahydrofuran. The above reaction is preferably carried out at temperatures between about 0° and about 50° C.

Mixtures of isomers which are obtained can be separated by chromatographic methods or by crystallization.

Compounds of formula I in which R signifies the group —CH$_2$—CH$_2$—R' and R' has the above significance can be manufactured by reduction, e.g. by catalytic hydrogenation or by reduction with diimide, of a compound of formula Ia in accordance with process variant c). The catalytic hydrogenation is effected according to methods which are known per se and which are familiar to any person skilled in the art. As catalysts there are preferably used noble metal catalysts, especially platinum catalysts, e.g. 5 percent palladium on active charcoal. As solvents there are preferably used lower fatty acid esters such as ethyl acetate, lower alcohols such as methanol and ethanol and open-chain or cyclic ethers such as diethyl ether, t-butyl methyl ether and tetrahydrofuran. The hydrogenation is preferably carried out under normal pressure or slightly thereover. The reaction temperature preferably lies in a range from about 0° to about 50° C., preferably at about room temperature.

The reduction with diimide is carried out in a manner known per se by preparing the diimide in situ from the dipotassium salt of azodicarboxylic acid and an acid, for example a lower fatty acid such as acetic acid. In this case there is used a polar solvent preferably a lower alcohol such as methanol and ethanol. The reaction temperature preferably lies between about −10° and about 30° C.

The compounds of formula II which are used as starting materials can be prepared in accordance with the following Reaction Schemes I and II; therein Ra signifies a saturated or partially unsaturated hydrocarbon group with up to 14 carbon atoms or an aryl, heteroaryl, arylcarbonyl or heteroarylcarbonyl group attached via an alkyl or alkenyl group with up to 6 carbon atoms and R' has the above significance.

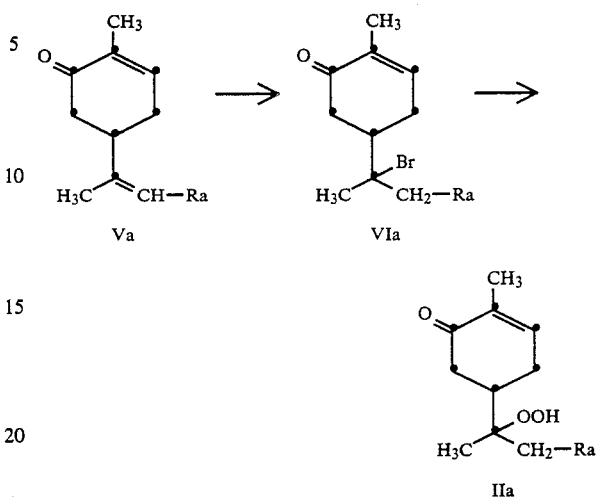

The conversion of a compound of formula Va into a compound of formula VIa can be carried out by treatment with hydrogen bromide in the presence of a catalytic amount of a Lewis acid such as zinc bromide in an organic solvent. Especially suitable solvents are halogenated lower hydrocarbons such as methylene chloride. This hydrobromination is preferably effected in a temperature range from about 0° C. to about room temperature.

The conversion of a compound of formula VIa into a compound of formula IIa can be carried out by treatment with 100 percent hydrogen peroxide in the presence of silver salts such as silver trifluoroacetate in an inert organic solvent. Especially suitable solvents are openchain and cyclic ethers such as diethyl ether, t-butyl methyl ether and tetrahydrofuran. The reaction is preferably carried out in a range from about 0° C. to about room temperature.

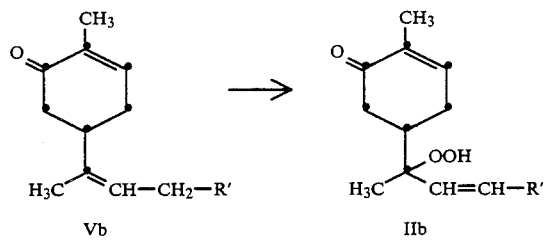

The conversion of a compound of formula Vb into a compound of formula IIb can be carried out in a manner known per se by singlet oxygen oxidation. This reaction is preferably carried out in a suitable organic solvent while introducing oxygen or air in the presence of a colouring substance such as e.g. methylene blue, bengal rose or tetraphenylporphyrin and while irradiating with a lamp. Suitable solvents are e.g. halogenated lower hydrocarbons such as methylene chloride, lower alcohols such as methanol and ethanol lower fatty acid esters such as ethyl acetate and acetonitrile. The reaction is preferably carried out in a temperature range from about −50° C. to about room temperature.

In the above processes for the preparation of compounds of formula II it is not necessary to isolate them. They can be converted directly into compounds of formula I by adding the cyclizing catalyst, preferably an acid, especially p-toluenesulphonic acid, to the reaction solution obtained.

The compounds of formula III which are used as starting materials can be prepared from compounds of formula Ia in accordance with Reaction Scheme III hereinafter in which R' has the above significance.

Scheme III

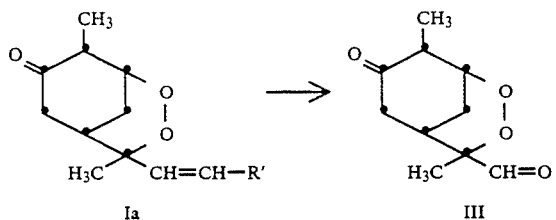

Ia                                III

The conversion of a compound of formula Ia into a compound of formula III can be carried out, for example, by oxidation with ozone. This is a reaction which is known per se and which is familiar to any person skilled in the art. As the solvent there is preferably used a lower alcohol such as methanol or a lower halogenated hydrocarbon such as methylene chloride. The reaction is preferably carried out at low temperatures, for example at about −70° C. A compound of formula Ia in which R' signifies hydrogen is preferably used as the starting material.

The compounds of formulae II and III are novel and are likewise objects of the present invention.

The remaining compounds which are used as starting materials are known or can be prepared in analogy to the known representatives of these classes of substance. In particular, the compounds in question can be prepared starting from (5S)-(+)-carvone or (5R)-(−)-carvone according to processes known per se. The Examples which follow below contain detailed information concerning the preparation of the starting materials in question.

As mentioned earlier, the compounds of formula I possess valuable pharmacological properties. They exhibit a pronounced activity against the causative organism of malaria. They have a pronounced blood schizontocidal activity. The activity of the substances in accordance with the invention can be determined, for example, in the animal experiment described hereinafter:

Male albino mice weighing 18–20 g are used as the experimental animals. They are kept in climatized rooms at 22°–23° C. in groups of 5 animals per cage. They receive ad libitum a diet feed with low PABA content and drinking water.

On the first day of the experiment (DO) the experimental animals are infected with Plasmodium berghey by intravenously injecting into each of the experimental animals 0.2 ml of heparinized blood of infected donor mice. The donor blood is diluted so that it contains $10^7$ parasitized erythrocytes per 0.2 ml. In untreated control animals the parasitemia normally reaches 70–80% on the fourth day after the infection (D+4) and the experimental animals die between days +5 to +8.

The substances to be tested are dissolved or suspended in distilled water or in a mixture of Tween 80, alcohol (96%) and water. Generally, in each case 0.5 ml of this solution or suspension is administered subcutaneously to groups of 5 experimental animals. The treatment is effected for the first time 3 hours after the infection as well as on the three subsequent days. Suitable dilutions of the test compounds are used for the titration of the activity. Per experiment 10 animals are treated in the same manner with the solution or suspension medium.

24 hours after the last treatment (D+4) blood smears with blood from tail veins are prepared from all animals and stained with giemsa. The average erythrocyte infection rate (parasitemia in %) in the control group as well as in the groups which have been treated with the compounds to be tested is determined by counting under the microscope. The difference in the average value of the infection rate between control group (100%) and the treated groups is calculated and expressed as the percentage reduction. The $ED_{50}$ is determined mathematically from the results obtained. The $ED_{50}$ in mg/kg is that dosage which, after four-fold administration, reduces to 50% the average erythrocyte infection rate in comparison to the control group.

The results which have been obtained with representative members of the class of substance defined by formula I in the previously described experiment are compiled in the following Table. Moreover, the Table contains data concerning the toxicity of some of these compounds. No toxic symptoms could be observed in the case of the single oral administration of the amounts indicated in the Table to mice.

TABLE

| Compound of formula I | | Activity $ED_{50}$ in | Toxicity Dosage in |
|---|---|---|---|
| R | Configuration | mg/kg s.c. | mg/kg p.o. |
| —(CH$_2$)$_7$—CH$_3$ | 1R, 4S, 5S, 8R | 5.2 | |
| " | 1R, 4R, 5S, 8R | 6.4 | |
| —(CH$_2$)$_8$—CH$_3$ | 1R, 4S, 5S, 8R | 6.0 | |
| " | 1R, 4R, 5S, 8R | 3.6 | |
| —(CH$_2$)$_9$—CH$_3$ | 1R, 4S, 5S, 8R | 3.4 | |
| " | 1R, 4R, 5S, 8R | 5.2 | |
| —(CH$_2$)$_{10}$—CH$_3$ | 1R, 4S, 5S, 8R | 3.4 | 3000 |
| " | 1R, 4R, 5S, 8R | 5.2 | 3000 |
| " | 1S, 4R, 5R, 8S | 4.6 | |
| " | 1S, 4S, 5R, 8S | 5.9 | |
| —CH=CH—(CH$_2$)$_7$—CH$_3$ | 1R, 4R, 5S, 8R, | 6.2 | |
| " | 1R, 4S, 5S, 8R | 4.5 | |

TABLE-continued

| Compound of formula I | | Activity ED$_{50}$ in mg/kg s.c. | Toxicity Dosage in mg/kg p.o. |
| --- | --- | --- | --- |
| R | Configuration | | |
|  | 1R, 4S, 5S, 8R<br>1S, 4R, 5R, 8S | 6.2<br>5.4 | 6000 |
| 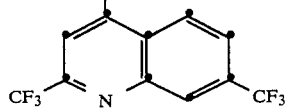 | 1S, 4R, 5R, 8S | 4.6 | |

The compounds of formula 1 can be used as medicaments, e.g. in the form of pharmaceutical preparations for enteral or parenteral administration. They can be administered, for example, perorally, e.g. in the form of tablets, coated tablets, dragees, hard and soft gelatine capsules, solutions, emulsions or suspensions, rectally, e.g. in the form of suppositories, or parenterally, e.g. in the form of injection solutions.

The manufacture of the pharmaceutical preparations can be effected in a manner which is familiar to any person skilled in the art by bringing the described compounds of formula I, optionally in combination with other therapeutically valuable substances, into a galenical administration form together with suitable, non-toxic, inert, therapeutically compatible solid or liquid carrier materials and, if desired, the usual pharmaceutical adjuvants.

As carrier materials there are suitable not only inorganic carrier materials, but also organic carrier materials. Thus, for tablets, coated tablets, dragees and hard gelatine capsules there can be used as carrier materials, for example, lactose, maize starch or derivatives thereof, talc, stearic acid or its salts. Suitable carrier materials for soft gelatine capsules are, for example, vegetable oils, waxes, fats and semi-solid and liquid polyols (depending on the nature of the active substance no carriers are, however, required in the case of soft gelatine capsules). Suitable carrier materials for the manufacture of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants there come into consideration the usual stabilizing, preserving, wetting and emulsifying agents, flavour-improving agents salts for varying the osmotic pressure, buffer substances, solubilizers, colouring and coating agents and antioxidants.

The dosing of the compounds of formula I can vary within wide limits depending on the parasites to be controlled, the age and the individual condition of the patient and on the mode of administration and will, of course, be fitted to the individual requirements in each particular case. For the prevention and treatment of malaria there comes into consideration for adult patients a daily dosage of about 0.01 g to about 4 g, especially about 0.05 g to about 2 g. Depending on the dosing it is convenient to administer the daily dosage in several unit dosages.

The pharmaceutical preparations conveniently contain about 10–1000 mg preferably 50–500 mg, of a compound of formula I.

The following Examples serve to illustrate the present invention in more detail. However, they are not intended to limit its scope in any manner. All temperatures are given in degrees Celsius.

EXAMPLE 1

(a) A solution of 941 g of 3-chloroperbenzoic acid (55%) in 9 l of methylene chloride is cooled in an ice bath. 360 ml of (5S)-(+)-carvone are added dropwise thereto so that the temperature does not rise above 20°. The reaction mixture is stirred at room temperature for 3.5 hours. whereby a precipitate of 3-chlorobenzoic acid forms. This suspension is stirred for 30 minutes and cooled with ice in order to complete the precipitation. The precipitate is filtered off and washed with hexane/methylene chloride (9:1). The filtrate is evaporated carefully. The thus-obtained oil (epoxide) is suspended in 3 l of ice-water and treated with 180 ml of 3N sulphuric acid while cooling in an ice bath so that the temperature does not rise above 20°. The mixture is stirred at room temperature for 15 hours. The pH is adjusted to 6.5 by adding 180 ml of 3N sodium hydroxide solution. A small amount of 3-chlorobenzoic acid is filtered off. The aqueous phase is cooled to 0°, whereupon 490 g of sodium (meta)periodate are added in portions over 30 minutes so that the temperature does not rise above 20°. After stirring at room temperature for 2 hours 30 g of sodium sulphite and 200 g of sodium bicarbonate are added in succession. The suspension is filtered and the filtrate is extracted three times with 3 l of methylene chloride each time. The combined organic phases are dried over sodium sulphate and evaporated. The crude product is crystallized from hexane/ethyl acetate at 0°. There is obtained (5S)-5-acetyl-2-methyl-2-cyclohexen-1-one. M.p. 35°; $[\alpha]_D^{25} = 81°$ (c=1 in ethanol).

(b) 44 g of n-butyltriphenylphosphonium bromide are suspended in 500 ml of dry tetrahydrofuran under argon and cooled to −50°. 69 ml of 1.33N n-butyllithium in hexane are added thereto. The orange coloured suspension is warmed to room temperature and then again cooled to −50°. 14 g of (5S)-5-acetyl-2-methyl-2-cyclohexen-1-one dissolved in 20 ml of dry tetrahydrofuran are added dropwise thereto over a period of 20 minutes. The cooling bath is then removed and the suspension is left to warm to room temperature. After stirring for 2 hours the reaction mixture is filtered through siliceous earth. The filtrate is evaporated, the dark residue is dissolved in 500 ml of ethyl acetate and washed twice with 200 ml of water each time. The organic phase is dried over sodium sulphate and evaporated. The thus-obtained oil is purified by column chromatography on silica gel with hexane/ethyl acetate (95:5) as the elution agent. There is obtained (5S)-2-methyl-5-[(Z)-1-methyl-1-pentenyl]-2-cyclohexen-1-one which still contains about 15% of the corresponding (E)-isomer.

$^1$H-NMR spectrum (CDCl$_3$): signals inter alia at 3.1 (m,1H). 5.2 (t,1H) and 6.75 (broad,1H) ppm.

(c) 2 g of (5S)-2-methyl-5-[(Z)-1-methyl-1-pentenyl]-2-cyclohexen-1-one are dissolved in 100 ml of methylene chloride and cooled to 0°. After adding a catalytic amount (100 mg) of zinc chloride the solution is saturated with hydrogen bromide gas. After 30 minutes the solution is filtered through 1 g of silica gel and evaporated carefully. The resulting oily residue of 2.8 g is dissolved in dry ether, cooled to 0° and treated with 1 ml of 100 percent hydrogen peroxide. 3.45 g of silver trifluoroacetate dissolved in 25 ml of dry ether are added dropwise over a period of 30 minutes. The excess of silver ions is precipitated by adding 1 ml of 1N hydrochloric acid and the suspension obtained is filtered through silica gel. In order to remove the excess hydrogen peroxide, the filtrate is washed five times with 10 ml of water each time. The ether phase is then evaporated carefully and the residue is taken up 100 ml of methanol. A catalytic amount of sodium methanolate (100 mg) is added to this solution, whereupon the mixture is left to stand at room temperature for 15 hours. The methanol is distilled off and the residue is purified and separated into the two diastereomers (1:1) by chromatography on silica gel while eluting with hexane/ethyl acetate (7:3). There are obtained (1R,4R,5S,8R)-4-butyl-4,8-dimethyl-2,3-dioxabicyclo[3.3.1]nonan-7-one [mass spectrum: peaks inter alia at m/e 227 (M$^+$ +1), 153 and 85; $[\alpha]_D^{25}$ = −137.5° (c=1 in methanol)]and (1R,4S,5S,8R)-4-butyl-4,8-dimethyl-2,3-dioxabicyclo[3.3.1]nonan-7-one [mass spectrum: peaks inter alia at m/e 227 (M$^+$ +1), 153 and 85].

In an analogous manner:

(d) by using (5R)-(−)-carvone in place of (5S)-(+)-carvone as the starting material there are obtained (1S,4R,5R,8S)4-butyl-4,8-dimethyl-2,3-dioxabicyclo[3.3.1]nonan-7-one [mass spectrum: peaks inter alia at m/e 227 (M$^+$ +1), 153 and 85] and (1S,4S,5R,8S)-4-butyl-4,8-dimethyl-2,3-dioxabicyclo[3.3.1]nonan-7-one [mass spectrum: peaks inter alia at m/e 227 (M$^+$ +1), 153 and 85];

(e) by using isopentyltriphenylphosphonium bromide in step (b) in place of n-butyltriphenylphosphonium bromide there are obtained (1R,4S,5S,8R)-4-isopentyl-4,8-dimethyl-2,3-dioxabicyclo[3.3.1]nonan-7-one [$^1$H-NMR spectrum (CDCl$_3$) signals inter alia at 0.9 (d,6H), 1.05 (d,3H) and 1.1 (s,3H) ppm] and (1R,4R,5S,8R)-4-isopentyl-4,8-dimethyl-2,3-dioxabicyclo[3.3.1]nonan-7-one [$^1$H-NMR spectrum (CDCl$_3$): signals inter alia at 0.8 (d,6H), 1.3 (d,3H) and 1.4 (s,3H) ppm];

(f) by using 3-phenylpropyltriphenylphosphonium bromide in step (b) in place of n-butyltriphenylphosphonium bromide there are obtained (1R,4S,5S,8R)-4,8-dimethyl-4-(3-phenylpropyl)-2,3-dioxabicyclo[3.3.1]nonan-7-one [mass spectrum (chemical ionization): peaks inter alia at m/e 256 (M$^+$ −32) and 104] and (1R,4R,5S,8R)-4,8-dimethyl-4-(3-phenylpropyl)-2,3-dioxabicyclo[3.3.1]nonan-7-one [mass spectrum (chemical ionization): peaks inter alia at m/e 306 (M$^+$ +NH$_4$), 273 (M$^+$ −15) and 180];

(g) by using (5R)-(−)-carvone as the starting material in place of (5S)-(+)-carvone and by using 3-phenylpropyltriphenylphosphonium bromide in step (b) in place of n-butyltriphenylphosphonium bromide there are obtained (1S,4R, 5R,8S)-4,8-dimethyl-4-(3-phenylpropyl)-2,3-dioxabicyclo[3.3.1]nonan-7-one [$^1$H-NMR spectrum (CDCl$_3$): signals inter alia at 0.9 (s,3H) and 7.2 (s,5H) ppm] and (1S,4S,5R,8S)-4,8-dimethyl-4-(3-phenylpropyl)-2,3-dioxabicyclo[3.3.1]nonan-7-one [$^1$H-NMR spectrum (CDCl$_3$): signals inter alia at 1.3 (s,3H) and 7.2 (s,5H) ppm];

(h) by the direct reaction of (5S)-(+)-carvone in accordance with step (c) there is obtained (1R,5S,8R)-4,4,8-trimethyl-2,3-dioxabicyclo[3.3.1]nonan-7-one [mass spectrum: peaks inter alia at m/e 184 (M$^+$), 126 and 85];

(i) by the direct reaction of (5R)-(−)-carvone in accordance with step (c) there is obtained (1S,5R,8S)-4,4,8-trimethyl-2,3-dioxabicyclo[3.3.1]nonan-7-one [mass spectrum: peaks inter alia at m/e 184 (M$^+$) and 85].

EXAMPLE 2

(a) 4.5 g of ethyltriphenylphosphonium bromide and 1.8 ml of N,N,N',N'-tetramethyl-ethylenediamine are cooled to 0° in 300 ml of tetrahydrofuran under argon. 7.5 ml of n-butyllithium (1.6M in hexane) are then added dropwise thereto while stirring and the mixture is stirred for a further 1 hour without cooling with ice. The red solution is cooled to −70°, whereupon 1.52 g of (S)-5-acetyl-2-methyl- 2-cyclohexen-1-one dissolved in 10 ml of tetrahydrofuran are added dropwise thereto during 15 minutes. The cooling bath is removed and the mixture is stirred for a further 45 minutes. After adding 20 ml of water the mixture is evaporated. The residue is taken up in ether and extracted twice with 0.3N sulphuric acid and twice with saturated sodium chloride solution. The ether phase is dried over sodium sulphate and evaporated. The crude product is purified by flash chromatography on silica gel while eluting with hexane/methylene chloride (1:1). There is obtained (5S)-2-methyl-5-[(Z)-1-methylpropenyl]-2-cyclohexen-1-one as a colourless oil [mass spectrum: peaks inter alia at m/e 164 (M$^+$), 149 (M$^+$ −15,CH$_3$), 135 (M$^+$ −29,COH), 82 and 54].

48 g of (5S)-2-methyl-5-[(Z)-1-methylpropenyl]-2-cyclohexen-1-one and 150 mg of methylene blue dissolved in 400 ml of acetonitrile are illuminated at 0° for 22 hours under a slight O$_2$ stream in a photooxidator equipped with a 600W white light lamp, a rotary stirrer and a cryostat condenser (−30°). The reaction mixture is removed from the apparatus, treated with 1 g of toluene-4-sulphonic acid and stirred at room temperature for 2 hours. After adding 20 ml of dimethyl sulphide the reaction mixture is evaporated carefully and the residue is purified by column chromatography on silica gel with methylene chloride as the elution agent. There is obtained (1R,4RS,5S,8R)-4.8-dimethyl-4-vinyl-2,3-dioxabicyclo[3.3.1]nonan-7-one as a colourless oil [mass spectrum (chemical ionization): peaks inter alia at m/e 214 (M$^+$ +NH$_4$) and 197 (M$^+$ +1)].

The reaction mixture obtained after the illumination contains (5S)-5-[(RS)-2-hydroperoxy-3-buten-2-yl]-2- methyl-2-cyclohexen-1-one which, by evaporation and flash chromatography of the residue on silica gel while eluting with hexane/ethyl acetate (3:1), can be isolated and purified [mass spectrum (chemical ionization): peaks inter alia at m/e 214 (M$^+$+NH$_4$), 198 179 and 163].

Starting from corresponding starting materials, which are obtained in accordance with steps (a) and (b) of Example 1 with the changes indicated in each case, there are obtained in an analogous manner:

(b) (1R,4RS,5S,8R)-4-[(E)-1-butenyl]-4,8-dimethyl-2,3-dioxabicyclo[3.3.1]nonan-7-one [$^1$H-NMR spectrum (CDCl$_3$): signals inter alia at 5.55 (m,2H) and 4.25 (broad,1H) ppm; mass spectrum (chemical ionization): peaks inter alia at m/e 242 (M$^+$+NH$_4$), 144 and 116].

(c) by using octyltriphenylphosphonium bromide in step (b) of Example 1 in place of n-butyltriphenylphosphonium bromide (1R,4R,5S,8R)-4,8-dimethyl-4-[(E)-1-octenyl]-2,3-dioxabicyclo[3.3 1]nonan-7-one [mass spectrum: peaks inter alia at m/e 155 and 71] and (1R,4S,5S,8R)-4,8-dimethyl-4-(E)-1-octenyl]-2.3-dioxabicyclo3.3.1]nonan-7-one [mass spectrum: peaks inter alia at m/e 249, 139, 55 and 43];

(d) by using nonyltriphenylphosphonium bromide in step (b) of Example 1 in place of n-butyltriphenylphosphonium bromide (1R,4R,5S,8R)-4,8-dimethyl-4-[(E)-1-nonenyl]-2,3-dioxabicyclo[3.3.1]nonan-7-one [$^1$H-NMR spectrum (CDCl$_3$): signals inter alia at 1.10 (s,3H), 4.35 (m,1H) and 5.2–6.0 (m,2H) ppm] and (1R,4S,5S,8R)-4,8-dimethyl-4-[(E)-1-nonenyl]-2.3-dioxabicyclo[3.3.1]nonan-7-one [mass spectrum: peaks inter alia at m/e 169 and 71];

(e) by using decyltriphenylphosphonium bromide in step (b) of Example 1 in place of n-butyltriphenylphosphonium bromide (1R,4R,5S,8R)-4-[(E)-1-decenyl]-4,8-dimethyl-2,3-dioxabicyclo[3.3.1]nonan-7-one [mass spectrum: peaks inter alia at m/e 309 (M$^+$+1) and 71] and (1R,4S,5S,8R)-4-[(E)-1-decenyl]-4,8-dimethyl-2,3-dioxabicyclo[3.3.1]nonan-7-one [mass spectrum: peaks inter alia at m/e 183 and 71];

(f) by using undecyltriphenylphosphonium bromide in step (b) of Example 1 in place of n-butyltriphenylphosphonium bromide (1R,4R,5S,8R)-4,8-dimethyl-4-[(E)-1-undecenyl]-2,3-dioxabicyclo[3.3.1]nonan-7-one [mass spectrum: peaks inter alia at m/e 236, 197, 181 and 71] and (1R,4S,5S,8R)-4,8-dimethyl-4-[(E)-1-undecenyl]-2,3-dioxabicyclo[3.3.1]-nonan-7-one [mass spectrum: peaks inter alia at m/e 304 (M$^+$−18, H$_2$O), 197, 55 and 43];

(g) by using (5R)-(−)-carvone as the starting material in step (a) of Example 1 in place of (5S)-(+)-carvone and by using undecyltriphenylphosphonium bromide in step (b) of Example 1 in place of n-butyltriphenylphosphonium bromide (1S,4S,5R,8S)-4,8-dimethyl-4-[(E)-1-undecenyl]-2,3-dioxabicyclo[3.3.1]nonan-7-one [mass spectrum: peaks inter alia at m/e 236, 197, 181 and 71] and (1S,4R,5R,8S)-4,8-dione [mass spectrum: peaks inter alia at m/e 304 (M$^+$−18, H$_2$O), 197, 55 and 43];

(h) by using dodecyltriphenylphosphonium bromide in step (b) of Example 1 in place of n-butyltriphenylphosphonium bromide (1R,4R,5S,8R)-4-[(E)-1-dodecenyl]-4,8-dimethyl-2,3-dioxabicyclo[3.3.1]nonan-7-one [mass spectrum: peaks inter alia at m/e 211 and 71] and (1R,4S,5S,8R)-4-[(E)-1-dodecenyl]-4,8-dimethyl-2,3-dioxabicyclo[3.3.1]nonan-7-one [mass spectrum: peaks inter alia at m/e 318 (M$^+$−18), 211 and 71];

(i) by using tetradecyltriphenylphosphonium bromide in step (b) of Example 1 in place of n-butyltri- phenylphosphonium bromide (1R,4R,5S,8R)-4,8-dimethyl-4-[(E)-1-tetradecenyl]-2,3-dioxabicyclo[3.3.1]nonan-7-one [mass spectrum: peaks inter alia at m/e 288, 239 and 71]and (1R,4S,5S,8R)-4,8-dimethyl-4-[(E)-1-tetradecenyl]-2,3-dioxabicyclo[3.3.1]nonan-7-one [mass spectrum: peaks inter alia at m/e 346 (M$^+$−18,H$_2$O), 332 (M$^+$−32,O$_2$), 239 and 71].

EXAMPLE 3

(a) 3.59 g of (1R,4S,5S,8R)-4-[(E)-1-decenyl]-4,8-dimethyl-2,3-dioxabicyclo[3.3.1]nonan-7-one [obtained in accordance with Example 2(e)] dissolved in 180 ml of ethyl acetate are hydrogenated for about 1.25 hours with hydrogen over 360 mg of 5 percent platinum/charcoal at 1.013·10$^5$ Pa. The end point of the reaction is determined by gas-chromatographic analysis. The catalyst is then removed by filtration through diatomaceous earth and the filtrate is evaporated. The residue is purified by column chromatography on silica gel while eluting with hexane/ethyl acetate (3:1). There is obtained (1R,4S,5S,8R)-4-decyl-4,8-dimethyl-2,3-dioxabicyclo[3.3.1]-nonan-7-one as a colourless oil, which crystallizes from hexane [m.p. 57°].

In an analogous manner:

(b) From the first product of Example 2(c) there is obtained (1R,4S,5S,8R)-4,8-dimethyl-4-octyl-2,3-dioxabicyclo[3.3.1]nonan-7-one [m.p. 41°];

(c) from the second product of Example 2(c) there is obtained (1R,4R,5S,8R)-4,8-dimethyl-4-octyl-2,3-dioxabicyclo[3.3.1]nonan-7-one [m.p. 27°];

(d) from the first product of Example 2(d) there is obtained (1R,4S,5S,8R)-4,8-dimethyl-4-nonyl-2,3-dioxabicyclo[3.3.1]nonan-7-one [m.p. 39°];

(e) from the second product of Example 2(d) there is obtained (1R,4R,5S,8R)-4,8-dimethyl-4-nonyl-2,3-dioxabicyclo[3.3.1]nonan-7-one [m.p. 40°];

(f) from the first product of Example 2(e) there is obtained (1R,4R,5S,8R)-4-decyl-4,8-dimethyl-2,3-dioxabicyclo[3.3.1]nonan-7-one [m.p. 40°];

(g) from the second product of Example 2(f) there is obtained (1R,4S,5S,8R)-4,8-dimethyl-4-undecyl-2,3-dioxabicyclo[3.3.1]nonan-7-one [m.p. 56°; $[\alpha]_D^{25}$ = −158.8 (c=1 in ethanol)];

(h) from the first product of Example 2(f) there is obtained (1R,4R,5S,8R)-4,8-dimethyl-4-undecyl-2,3-dioxabicyclo[3.3.1]nonan-7-one [m.p. 42°; $[\alpha]_D^{25}$ = −157.7 (c=1 in ethanol)];

(i) from the second product of Example 2(g) there is obtained (1S,4R,5R,8S)-4,8-dimethyl-4-undecyl-2,3-dioxabicyclo[3.3.1]nonan-7-one [m.p. 56°];

(j) from the first product of Example 2(g) there is obtained (1S,4S,5R,8S)-4,8-dimethyl-4-undecyl-2,3-dioxabicyclo[3.3.1]nonan-7-one [m.p. 42°];

(k) from the second product of Example 2(h) there is obtained (1R,4S,5S,8R)-4-dodecyl-4,8-dimethyl-2,3-dioxabicyclo[3.3.1]nonan-7-one [m.p. 67°];

(l) from the first product of Example 2(h) there is obtained (1R,4R,5S,8R)-4-dodecyl-4,8-dimethyl-2,3-dioxabicyclo[3.3.1]nonan-7-one [m.p. 35°];

(m) from the second product of Example 2(i) there is obtained (1R,4S,5S,8R)-4,8-dimethyl-4-tetradecyl-2,3-dioxabicyclo[3.3.1]nonan-7-one [m.p. 74°]:

(n) from the first product of Example 2(i) there is obtained (1R,4R,5S,8R)-4,8-dimethyl-4-tetradecyl-2,3-dioxabicyclo[3.3.1]nonan-7-one [m.p. 46°].

EXAMPLE 4

(a) 33 g of (1R,4RS,5S,8R)-4,8-dimethyl-4-vinyl-2,3-dioxabicyclo[3.3.1]nonan-7-one [obtained in accordance with Example 2(a)] are dissolved in 100 ml of methanol and cooled to −70° under argon. A stream of ozone from 40 1 of oxygen/h is introduced and maintained up to saturation (pale blue colour). After 3–4 hours the source of current is switched off and the excess ozone is displaced by oxygen. 40 ml of dimethyl sulphide are added thereto and the suspension is then allowed to warm to room temperature. The methanol is distilled off and the residue is purified and separated by column chromatography on silica gel while eluting with hexane/ethyl acetate (2:1 to 1:2). After crystallization from hexane/ethyl acetate at 0° there are obtained (1R,4R,5S,8R)-4,8-dimethyl-7-oxo-2,3dioxabicyclo[3.3.1]nonane-4-carboxaldehyde [m.p. 92°] and (1R,4S,5S,8R)-4,8-dimethyl-7-oxo-2,3-dioxabicyclo[3.3.1]-nonane-4-carboxaldehyde [m.p. 97°].

(b) 760 mg of (1R,4S,5S,8R)-4,8-dimethyl-7-oxo-2,3-dioxabicyclo[3.3 1]nonane-4-carboxaldehyde are dissolved in 80 ml of methylene chloride. 2.5 g of 2,7-bis(trifluoromethyl)quinolin-4-yl-methylidenetriphenylphosphorane are added thereto and the solution is left to stand at room temperature for 24 hours. The methylene chloride is distilled off and the residue is separated into the (E)- and (Z)-isomers by column chromatography on silica gel while eluting with methylene chloride. After crystallization from hot methanol there are obtained (1R,4S,5S, 8R)-4-[(Z)-2-[2,7-bis(trifluoromethyl)-4-quinolinyl]vinyl]-4,8-dimethyl-2,3-dioxabicyclo[3.3.1-]nonan-7-one as white crystals [m.p. 160°; $[\alpha]_D^{25}=53.7°$ (c=1 in ethanol)]and (1R,4S,5S,8R)-4-[(E)-2-[2,7-bis(trifluoromethyl) -4-quinolinyl]vinyl]-4,8-dimethyl-2,3-dioxabicyclo[3.3.1]nonan-7-one [m.p. 188°].

In an analogous manner:

(c) By using a corresponding starting material prepared from (5R)-(−)-carvone there is obtained (1S,4R,5R,8S)-4-[(Z)-2-[2,7-bis(trifluoromethyl)-4-quinolinyl]vinyl]-4,8-dimethyl-1,3-dioxabicyclo[3.3.1-]nonan-7-one m.p. 160°];

(d) by using p-trifluoromethylbenzylidenetriphenylphosphorane prepared in situ by means of p-trifluoromethylbenzyltriphenylphosphonium bromide and sodium bis-(trimethylsilyl)amide there is obtained (1R,4R,5S,8R)-4,8-dimethyl-4-[(E)-4-(trifluoromethyl)-styryl]-2,3-dioxabicyclo[3.3.1]nonan-7-one [mass spectrum: peaks inter alia at m/e 321 (M+−19,F) and 85];

(e) by using p-chlorophenacylidenetriphenylphosphorane prepared in situ by means of p-chlorophenacyltriphenylphosphonium bromide and sodium ethylate there is obtained (1R,4S,5S,8R)-4-[(E)-2-(4-chlorobenzoyl)vinyl]-4,8-dimethyl-2,3-dioxabicyclo[3.3.1]nonan-7-one [m.p. 127°];

(f) by using 2-(1-adamantyl)ethylidenetriphenylphosphorane prepared in situ by means of 2-(1-adamantyl)ethyltriphenylphosphonium bromide and n-butyllithium there is obtained (1R,4R,5S,8R)-4-[(Z)-3-(1-adamantyl)-propenyl]- 4,8-dimethyl-2,3-dioxabicyclo[3.3.1]nonan-7-one [m.p. 146° (decomposition)];

(g) by using geranylidenetriphenylphosphorane prepared in situ by means of geranyltriphenylphosphonium bromide and n-butyllithium there are obtained (1R,4R,5S,8R)-4-[(all-Z)-4,8-dimethyl-1,3,7-nonatrienyl]-4,8-dimethyl-2,3-dioxabicyclo[3.2.1]nonan-7-one [mass spectrum: peaks inter alia at m/e 318 (M+) and 69] and (h) (1R,4S,5S,8R)-4-[(1Z,3E)-4,8-dimethyl-1,3,7-nonatrienyl]-4,8-dimethyl-2,3-dioxabicyclo[3.2.1]nonan-7-one [mass spectrum: peaks inter alia at m/e 249 and 69];

(i) by using a corresponding starting material prepared from (5R)-(−)-carvone and 2,8-bis(trifluoromethyl)-quinolin-4-yl-methylidenetriphenylphosphorane there is obtained (1S,4R,5R,8S)-4-[(Z)-2-[2,8-bis-(trifluoromethl)-4-quinolinyl]vinyl]-4,8-dimethyl-2,3-dioxabicyclo-[3.3.1]nonan-7-one [m.p. 137°];

(k) by using a corresponding starting material prepared from (5R)-(−)-carvone and 6,8-dichloro-2-trifluoromethyl-4-quinolinyl-methylidenetriphenylphosphorane there are obtained (1S,4R,5R,8S)-4-[(E)-2-[6,8-dichloro-2-(trifluoromethyl)-4-quinolinyl]vinyl]-4,8-dimethyl-2,3-dioxabicyclo[3.3.1]nonan-7-one [m.p. 196°] and (l) (1S,4R,5R,8S)-4-[(Z)-2-[6,8-dichloro-2-(trifluoromethyl)-4-quinolinyl]vinyl]-4,8-dimethyl-2,3-dioxabicyclo[3.3.1]nonan-7-one [m.p. 191°];

(m) by using 2.4-dichlorobenzylidenetriphenylphosphorane prepared by means of 2,4-dichlorobenzyltriphenylphosphonium chloride and n-butyllithium there is obtained (1R,4R,5S,8R)-4-[(Z)-2,4-dichlorostyryl]-4,8-dimethyl-2,3-dioxabicyclo[3.3.1]nonan-7-one [mass spectrum (chemical ionization): peaks inter alia at m/e 358 (M+ +NH4) and 179];

(n) by using 3,4-dichlorobenzylidenetriphenylphosphorane prepared by means of 3,4-dichlorobenzyltriphenylphosphonium chloride and sodium bis(trimethylsilyl)amide there is obtained (1R,4S,5S,8R)-4-[(Z)-3,4-dichlorostyryl]-4,8-dimethyl-2,3-dioxabicyclo[3.3.1]nonan-7-one [m.p. 135°];

(o) by using a corresponding starting material prepared from (5R)-(−)-carvone and 2,4-dichlorobenzylidenetriphenylphosphorane prepared by means of 2,4-dichlorobenzyltriphenylphosphonium bromide and sodium bis(trimethylsilyl)amide there is obtained (1S,4R,5R,8S)-4-[(Z)-2,4-dichlorostyryl]-4,8-dimethyl-2,3-dioxabicyclo[3.3.1]nonan-7-one [m.p. 137°];

(p) by using a corresponding starting material prepared from (5R)-(−)-carvone and 1-naphthylmethylidenetriphenylphosphorane prepared by means of 1-naphthylmethylenetriphenylphosphonium bromide and sodium bis(trimethylsilyl)amide there is obtained (1S,4R, 5R,8S)-4,8-dimethyl-4-[(Z)-2-(1-naphthyl)-vinyl]-2,3-dioxabicyclo[3.3.1]nonan-7-one [mass spectrum: peaks inter alia at m/e 322 (M+) and 152];

(q) by using a corresponding starting material prepared from (5R)-(−)-carvone and 4-bromo-1-naphthylmethylidenetriphenylphosphorane prepared by means of 4-bromo-1-naphthylmethylenetriphenylphosphonium bromide and sodium bis(trimethylsilyl)amide there is obtained (1S,4R,5R,8S)4-[(Z)-2-(4-bromo-1-naphthyl)vinyl]-4,8-dimethyl-2,3-dioxabicyclo[3.3.1-]nonan-7-one [m.p. 167°].

(r) by using a corresponding starting material prepared from (5R)-(−)-carvone and benzylidenetriphenylphosphorane prepared by means of benzyltriphenylphosphonium bromide and sodium bis(trimethylsilyl)amide there is obtained (1S,4R,5R,8S)-4,8-dimethyl-4-[(Z)-styryl]-2,3-dioxabicyclo[3.3.1]nonan-7-one [m.p. 60°];

(s) by using a corresponding starting material prepared from (5R)-(−)-carvone and 4-fluorobenzylidenetriphenylphosphorane prepared by means of 4-fluorobenzyltriphenylphosphonium chloride and sodium bis(trimethylsilyl)amide there is obtained (1S,4R,5R,8S)-4-[(Z)-4-fluorostyryl]-4,8-dimethyl-2,3-dioxabicyclo[3.3.1]nonan-7-one [m.p. 84°];

(t) by using a corresponding starting material prepared from (5R)-(—)-carvone and 4-chlorobenzylidenetriphenylphosphorane prepared by means of 4-chlorobenzyltriphenylphosphonium chloride and sodium bis(trimethylsilyl)amide there is obtained (1S,4R,5R,8S)-4-[(Z)-4-chlorostyryl]-4,8-dimethyl-2,3-dioxabicyclo[3.3.1]nonan-7-one [m.p. 90°];

(u) by using a corresponding starting material prepared from (5R)-(—)-carvone and 4-methylbenzylidenetriphenylphosphorane prepared by means of 4-methylbenzyltriphenylphosphonium bromide and sodium bis(trimethylsilyl)amide there is obtained (1S,4R,5R,8S)-4,8-dimethyl-4-[(Z)-4-methylstyryl]-2,3-dioxabicyclo[3.3.1]nonan-7-one [mass spectrum: peaks inter alia at m/e 286 (M+) and 145];

(v) by using a corresponding starting material prepared from (5R)-(—)-carvone and 4-(trifluoromethyl)-benzylidenetriphenylphosphorane prepared by means of 4-(trifluoromethyl)benzyltriphenylphosphonium bromide and sodium bis(trimethylsilyl)amide there is obtained (1S,4R,5R,8S)-4,8-dimethyl-4-[(Z)-4-(trifluoromethyl)styryl]-2,3-dioxabicyclo[3.3.1]nonan-7-one [mass spectrum (chemical ionization): peaks inter alia at m/e 358 (M+ +NH4) and 340];

(w) by using a corresponding starting material prepared from (5R)-(—)-carvone and (3-trifluoromethyl)-benzylidenerriphenylphosphorane prepared by means of sodium bis(trimethylsilyl)amide there is obtained (1S,4R,5R,8S)4,8-dimethyl-4-[(Z)-3-(trifluoromethyl)-styryl]-2,3-dioxabicyclo[3.3.1]nonan-7-one [m.p. 101°];

(x) by using a corresponding starting material prepared from (5R)-(—)-carvone and 4-cyanobenzylidenetriphenylphosphorane prepared by means of 4-cyanobenzyltriphenylphosphonium bromide and sodium bis(trimethylsilyl)amide there is obtained 4-[(Z)-2-[(1S,4R,5R,8S)-4,8-dimethyl-7-oxo-2,3-dioxabicyclo[3.3.1]nonan-4-yl]vinyl]benzonitrile [m.p. 125°];

(y) by using a corresponding starting material prepared from (5R)-(—)-carvone and 4-(t-butyl)benzylidenetriphenylphosphorane prepared by means of 4-(t-butyl)benzyltriphenylphosphonium bromide and sodium bis(trimethylsilyl)amide there is obtained (1S,4R,5R,8S)-4-[(Z)-4-(t-butyl)styryl]-4,8-dimethyl-2,3-dioxabicyclo[3.3.1]nonan-7-one [m.p. 101°];

(z) by using a corresponding starting material prepared from (5R)-(—)-carvone and 4-phenylbenzylidenetriphenylphosphorane prepared by means of 4-phenylbenzyltriphenylphosphonium chloride and sodium bis(trimethylsilyl)amide there is obtained (1S,4R,5R,8S)-4-[(Z)-4-biphenylvinyl]-4,8-dimethyl-2,3-dioxabicyclo[3.3.1]nonan-7-one [m.p. 148°];

(aa) by using a corresponding starting material prepared from (5R)-(—)-carvone and 4-methoxybenzylidenetriphenylphosphorane prepared by means of 4-methoxybenzyltriphenylphosphonium chloride and sodium bis(trimethylsilyl)amide there is obtained (1S,4R,5R,8S)-4-[(E/Z)-4-methoxystyryl]-4,8-dimethyl-2,3-dioxabicyclo[3.3.1]nonan-7-one. E/Z ratio =1:3; [mass spectrum: peaks inter alia at m/e 302 (M+) and 161];

(bb) by using a corresponding starting material prepared from (5R)-(—)-carvone and 2,4-dichlorobenzylidenetriphenylphosphorane prepared by means of 2,4-dichlorobenzyltriphenylphosphonium chloride and sodium bis(trimethylsilyl)amide there is obtained (1S,4R,5R,8S)-4-[(Z)-2,4-dichlorstyryl]-4,8-dimethyl-2,3-dioxabicyclo[3.3.1]nonan-7-one [mass spectrum (chemical ionization): peaks inter alia at m/e 358 (M+ +NH4) and 179];

(cc) by using a corresponding starting material prepared from (5R)-(—)-carvone and 2,4-bis(trifluoromethyl)benzylidenetriphenylphosphorane prepared by means of 2,4-bis(trifluoromethyl)benzyltriphenylphosphonium bromide and sodium bis(trimethylsilyl)amide there is obtained (1S,4R,5R,8S)-4-[(Z)-2,4-bis(trifluoromethyl)styryl-4,8-dimethyl-2,3-dioxabicyclo[3.3.1]nonan-7-one [m.p. 124°];

(dd) by using a corresponding starting material prepared from (5R)-(—)-carvone and 2-chloro-4-(trifluoromethyl)-benzylidenetriphenylphosphorane prepared by means of 2-chloro-4-(trifluoromethyl)benzyltriphenylphosphonium chloride and sodium bis(trimethylsilyl)amide there is obtained (1S,4R,5R,8S)-4-(Z)-2-chloro-4-(trifluromethyl)-styryl]-4,8-dimethyl-2,3-dioxabicyclo[3.3.1]nonan-7-one [m.p. 160°];

(ee) by using a corresponding starting material prepared from (5R)-(—)-carvone and 3,5-bis(trifluoromethyl)benzylidenetriphenylphosphorane prepared by means of 3,5-bis(trifluoromethyl)benzyltriphenylphosphonium bromide and sodium bis(trimethylsilyl)amide there is obtained (1S,4R,5R,8S)-4-[(E/Z)-3,5-bis(trifluoromethyl)styryl]-4,8-dimethyl-2,3-dioxabicyclo[3.3.1]nonan-7-one. E/Z ratio=1:5; [mass spectrum: peaks inter alia at m/e 389 (M+ —F) and 267];

(ff) by using a corresponding starting material prepared from (5R)-(—)-carvone and 2-chloro-4-cyanobenzylidenetriphenylphosphorane prepared by means of 2-chloro-4-cyanobenzyltriphenylphosphonium bromide and sodium bis(trimethylsilyl)amide there is obtained 3-chloro-4-[(Z)-2-(1S,4R,5R,8S)-4,8-dimethyl-7-oxo-2,3-dioxabicyclo[3.3.1]nonan-4-yl]vinyl]benzonitrile [m.p. 155°];

(gg) by using a corresponding starting material prepared from (5R)-(—)-carvone and pentafluorobenzylidenetriphenylphoshorane prepared by means of pentafluorobenzyltriphenylphosphonium bromide and sodium bis(trimethylsilyl)amide there is obtained (1S,4R,5R,8S)-4,8-dimethyl-4-[(E)-2,3,4,5,6-pentafluorostyryl]-2,3-dioxabicyclo[3.3.1]nonan-7-one [m.p. 128°];

(hh) by using 2,4-dichlorobenzylidenetriphenylphosphorane prepared in situ by means of 2,4-dichlorobenzyltriphenylphosphonium chloride and sodium bis(trimethylsilyl)amide there is obtained (1R,4S,5S,8R)-4-[(Z)-2,4-dichlorostyryl]-4,8-dimethyl-2,3-dioxabicyclo[3.3.1]nonan-7-one m.p. 137°];

(ii) by using 2,4-bis(trifluoromethyl)benzylidenetriphenylphosphorane prepared in situ by means of 2,4-bis(trifluoromethyl)benzyltriphenylphosphonium bromide and sodium bis(trimethylsilyl)amide there is obtained (1R,4S,5S,8R)-4-[(Z)-2,4-bis(trifluoromethyl)styryl]-4,8-dimethyl-2,3-dioxabicyclo[3.3.1]nonan-7-one [m.p. 124°];

(jj) by using 2-chloro-4-(trifluoromethyl)benzylidenetriphenylphosphorane prepared in situ by means of 2-chloro-4-(trifluoromethyl)benzyltriphenylphosphonium chloride and sodium bis(trimethylsilyl)amide there is obtained (1R,4S,5S,8R)-4-[(Z)-2-chloro-4-(trifluoromethyl)styryl]-4,8-dimethyl-2,3-dioxabicyclo[3.3.1]nonan-7-one [m.p. 160°];

(kk) by using 3,5-dicyanobenzylidenetriphenylphosphorane prepared in situ by means of 3,5-dicyanobenzyltriphenylphosphonium bromide and sodium bis(trimethylsilyl)amide there is obtained 5-[(Z)-2-

(1R,4S,5S,8R)-4,8-dimethyl-7-oxo-2,3-dioxabicyclo[3.3.1]nonan-4-yl]vinyl]isophthalonitrile [m.p. 185°]:

(11) by using pentafluorobenzylidenetriphenylphosphorane prepared in situ by means of pentafluorobenzyltriphenylphosphonium bromide and sodium bis(trimethylsilyl)amide there is obtained (1R,4S,5S,8R)-4,8-dimethyl-4-[(E)-2,3,4,5,6-pentafluorostyryl]-2,3-dioxabicyclo[3.3.1]nonan-7-one [m.p. 128°].

EXAMPLE A 4,8-Dimethyl-4undecyl-2,3-dioxabicyclo[3.3.1]nonan-7-one can be formulated as the active substance according to methods known per se into pharmaceutical preparations of the following composition:

| 1. Tablets of 500 mg | |
|---|---|
| Active substance | 500 mg |
| Lactose powd. | 149 mg |
| Polyvinylpyrrolidone | 15 mg |
| Dioctyl sodium sulphosuccinate | 1 mg |
| Na carboxymethylstarch | 30 mg |
| Magnesium stearate | 5 mg |
| | 700 mg |
| 2. Tablets of 50 mg | |
| Active substance | 50 mg |
| Lactose powd. | 50 mg |
| Microcrystalline cellulose | 82 mg |
| Na carboxymethylstarch | 15 mg |
| Magnesium stearate | 3 mg |
| | 200 mg |
| 3. Capsules of 100 mg | |
| Active substance | 100.0 mg |
| Lactose powd. | 104.7 mg |
| Maize starch | 70.0 mg |
| Hydroxypropylmethylcellulose | 10.0 mg |
| Dioctyl sodium sulphosuccinate | 0.3 m |
| Talc | 12.0 mg |
| Magnesium stearate | 3.0 mg |
| | 300.0 mg |
| 4. Suppositories of 500 mg | |
| Active substance | 500 mg |
| Suppository mass | ad 2000 mg |
| 5. Soft gelatine capsules of 100 mg | |
| Active substance | 100 mg |
| Triglyceride medium chain | 300 mg |
| | 400 mg |

We claim:

1. Compounds of the formula

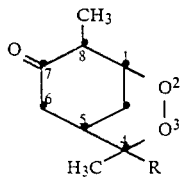

wherein R is a saturate or unsaturated hydrocarbon group with from 1 to 15 carbon atoms or an aryl, or arylcarbonyl group attached via a lower alkyl or lower alkenyl group.

2. The compounds of claim 1 wherein said compounds have the formula

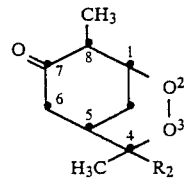

wherein $R_2$ is alkyl containing from 1 to 15 carbon atoms, alkenyl containing from 2 to 15 carbon atoms, cycloalkyl containing from 3 to 10 carbon atoms, cycloalkenyl containing from 3 to 10 carbon atoms, cycloalkylloweralkenyl, cycloalkylloweralkyl, cycloalkenylloweralkyl, cycloalkenylloweralkenyl., aryl containing 6 to 12 carbon atoms, arylloweralkyl, arylcarbonyl containing from 7 to 13 carbon atoms, arylloweralkenyl, arylcarbonylloweralkyl, or arylcarbonylloweralkenyl.

3. The compound of claim 2, wherein $R_2$ is alkyl containing 8 to 12 carbon atoms.

4. The compound of claim 3, wherein said compound is 4,8-dimethyl-4-octyl-2,3-dioxabicyclo[3.3.1]nonan-7-one.

5. The compound of claim 3, wherein said compound is 4,8-dimethyl-4-nonyl-2,3-dioxabicyclo[3.3.1]nonan-7-one.

6. The compound of claim 3, wherein said compound is 4-decyl-4,8-dimethyl-2,3-dioxabicyclo[3.3.1]nonan-7-one.

7. The compound of claim 3, wherein said compound is 4,8-dimethyl-4-undecyl-2,3-dioxabicyclo[3.3.1]-nonan-7-one.

8. The compound of claim 3, wherein said compound is 4-dodecyl 4,8-dimethyl-2,3-dioxabicyclo[3.3.1]-nonan-7-one.

9. The compound of claim 2, wherein $R_2$ is alkenyl containing from 2 to 15 carbon atoms.

10. The compound of claim 9, wherein said compound is 4,8-dimethyl-4-vinyl-2,3-dioxabicyclo[3.3.1-]nona-7-one.

11. The compound of claim 9, wherein said compound is 4-[1-butenyl]-4,8-dimethyl-2,3-dioxabicyclo[3.3.1]nonan-7-one.

12. The compound of claim 9, wherein said compound is 4,8-dimethyl-4-[1-octenyl]-2,3-dioxabicyclo[3.3.1]nonan-7-one.

13. The compound of claim 9, wherein said compound is 4,8-dimethyl-4-[1-nonenyl]-2,3-dioxabicyclo[3.3.1]nonan-7-one.

14. The compound of claim 9, wherein said compound is 4-[1-decenyl]-4,8-dimethyl-2,3-dioxabicyclo[3.3.1]-nonan-7-one.

15. The compound of claim 9, wherein said compound is 4,8-dimethyl-4-[1-undecenyl]2,3-dioxabicyclo[3.3.1]-nonan-7-one.

16. The compound of claim 9, wherein said compound is 4-[1-dodecenyl]-4,8-dimethyl-2,3-dioxabicyclo[3.3.1]nonan-7-one.

17. The compound of claim 9, wherein said compound is 4,8-dimethyl-4-[1-tetradecenyl]-2,3-dioxabicyclo[3.3.1]nonan-7-one.

18. The compound of claim 9, wherein said compound is 4-[4,8-dimethyl-1,3,7-nonatrienyl]-4,8-dimethyl-2,3-dioxabicyclo[3.2.1]nonan-7-one.

19. The compound of claim 2, wherein $R_2$ is cycloalkylloweralkenyl.

20. The compound of claim 19, wherein said compound is 4[3-(1-adamantyl)propenyl]-4,8-dimethyl-2,3-dioxabicyclo[3.3.1]nonan-7 one.

21. The compound of claim 2, wherein $R_2$ is arylloweralkyl.

22. The compound of claim 21, wherein said aryl is unsubstituted.

23. The compound of claim 22, wherein said compound 4,8-dimethyl-4-(3-phenylpropyl)-2,3-dioxabicyclo[3.3.1]nonan-7-one.

24. The compound of claim 2, wherein said compound is arylloweralkenyl.

25. The compound of claim 24, wherein said aryl is unsubstituted.

26. The compound of claim 25, wherein said compound is 4,8-dimethyl-4-[(2-(1-naphthyl)vinyl]-2,3-dioxabicyclo[3.3.1]nonan-7-one.

27. The compound of claim 25, wherein said compound is 4,8-dimethyl-4-[styryl]-2,3-dioxabicyclo-[3.3.1]nonan-7-one.

28. The compound of claim 24, wherein the aryl is substituted with a substituent selected from the group consisting of halogen, trifluoromethyl, phenyl, cyano, lower alkoxy, and lower alkyl.

29. The compound of claim 28, wherein said aryl is substituted with phenyl.

30. The compound of claim 29, wherein said compound is 4-[4-biphenylvinyl]-4,8-dimethyl-2,3-dioxabicyclo[3.3.1]nonan-7-one.

31. The compound of claim 28, wherein said aryl is substituted with halogen.

32. The compound of claim 31, wherein said aryl is napthyl.

33. The compound of claim 32, wherein said compound is 4-[2-(4-bromo-1-naphthyl)vinyl]-4,8-dimethyl-2,3-dioxabicyclo[3.3.1]nonan-7 one.

34. The compound of claim 31, wherein said aryl is phenyl.

35. The compound of claim 34, wherein said compound is 4-[2,4-dichlorostyryl]-4,8-dimethyl-2,3-dioxabicyclo[3.3.1]nonan-7-one.

36. The compound of claim 34, wherein said compound is 4-dichlorostyryl]-4,8-dimethyl-2,3-dioxabicyclo[3.3.1]nonan-7-one.

37. The compound of claim 34, wherein said compound is 4-[4-fluorostyryl]-4,8-dimethyl-2,3-dioxabicyclo[3.3.1]nonan-7-one.

38. The compound of claim 34, wherein said compound is 4-[4-chlorostyryl]-4,8-dimethyl-2,3-dioxabicyclo[3.3.1]nonan-7-one.

39. The compound of claim 34, wherein said compound is 4,8-dimethyl-4-[(2,3,4,5,6-pentafluorostyryl]-2,3-dioxabicyclo[3.3.1]nonan-7-one.

40. The compound of claim 28, wherein said aryl is substituted with trifluoromethyl.

41. The compound of claim 40, wherein said compound is 4,8-dimethyl-4-[4-(trifluoromethyl)styryl]-2,3-dioxabicyclo [3.3.1]nonan-7-one.

42. The compound of claim 40, wherein said compound is 4,8-dimethyl-4-[3-(trifluoromethyl)styryl]-2,3-dioxabicyclo [3 3.1]nonan-7-one.

43. The compound of claim 40, wherein said compound is 4-[2,4-bis(trifluoromethyl)styryl]-4,8-dimethyl-2,3-dioxabicyclo[3.3.1]nonan-7-one.

44. The compound of claim 40, wherein said compound is 4-[2-chloro-4-(trifluoromethyl)-styryl]-4,8-dimethyl-2,3-dioxa bicyclo[3.3.1]nonan-7-one.

45. The compound of claim 40, wherein said compound is 3,5-bis(trifluoromethyl)styryl]-4,8-dimethyl-2,3-dioxabicyclo [3.3.1]nonan-7-one.

46. The compound of claim 28, wherein said aryl is substituted with lower alkyl.

47. The compound of claim 46, wherein said compound is 4,8-dimethyl-4[4-methylstyryl]-2,3-dioxabicyclo[3.3.1]nonan-7one.

48. The compound of claim 46, wherein said compound is 4-[4-(t-butylstyryl]-4,8-dimethyl-2,3-dioxabicyclo[3.3.1]nonan-7-one.

49. The compound of claim 28, wherein said aryl is substituted with lower alkoxy.

50. The compound of claim 49, wherein said compound is 4-[4-methoxystyryl]-4,8-dimethyl-2,3-dioxabicyclo[3.3.1]nonan-7-one.

51. The compound of claim 28, wherein said aryl is substituted with cyano.

52. The compound of claim 51, wherein said compound is 3-chloro-4-[2-[4,8-dimethyl-7-oxo-2,3-dioxabicyclo[3.3.1]nonan-4-yl]vinyl]benzonitrile.

53. The compound of claim 51, wherein said compound is 5-[2-[4,8-dimethyl-7-oxo-2,3-dioxabicyclo[3.3.1]nonan-4-yl]-vinyl]isophthalonitrile.

54. The compound of claim 2, wherein $R_2$ is arylcarbonylloweralkenyl.

55. The compound of claim 54, wherein said compound is 4-[2-(4-chlorobenzoyl)vinyl]-4,8-dimethyl-2,3-dioxabicyclo [3.3.1]nonan-7-one.

56. A method of combatting malaria comprising administering to a patient an effective amount of a compound of the formula

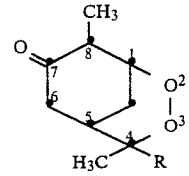

I wherein R is a saturated or unsaturated hydrocarbon group with from 1 to 15 carbon atoms or an aryl, heteroaryl, arylcarbonyl or heteroaryl-carbonyl group attached via an alkyl or alkenyl group with from 1 to 7 carbon atoms in a therapeutically inert carrier material.

57. A pharmaceutical composition comprising a compound of the formula

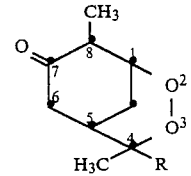

I wherein R is a saturated or unsaturated hydrocarbon group with from 1 to 15 carbon atoms or an aryl, heteroaryl, arylcarbonyl or heteroaryl-carbonyl group attached via an alkyl or alkenyl group with from 1 to 7 carbon atoms and a therapeutically inert carrier material.

58. A compound of the formula

59. A compound of the formula

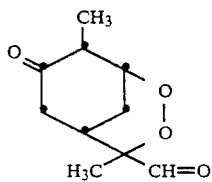

60. Compounds of the formula:

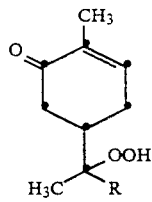

wherein R is a saturated or unsaturated hydrocarbon group with from 1 to 15 carbon atoms or an aryl, heteroaryl, arylcarbonyl or heteroarylcarbonyl group attached via an alkyl or alkenyl group with from 1 to 7 carbon atoms.

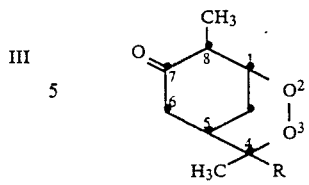

wherein R is a heteroaryl or a heteroarylcarbonyl group attached via a lower alkyl or lower alkenyl groups.

61. The compound of claim 1 wherein said compounds have the formula:

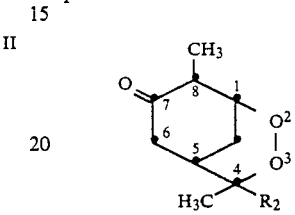

wherein $R_2$ is a selected from the group consisting of heteroaryl, heteroarylcarbonyl, heteroarylloweralkyl, heretoalkylloweralkenyl, heteroarylcarbonylloweralkyl and heterarylcarbonylloweralkenyl where the heteroaryl moiety in said heteroaryl substituent contains a mono or bicyclic ring structure with from 5 to 12 members in said ring structure and from 1 to 3 nitrogen atoms as the only hetero atom in said ring structure with each ring in said ring structure containing from 5 to 6 ring members.

* * * * *

UNITED STATES PATENT AND TRADEMARK OFFICE
CERTIFICATE OF CORRECTION

PATENT NO. : 4,977,184
DATED : December 11, 1990
INVENTOR(S) : HOFHEINZ ET AL.

It is certified that error appears in the above-identified patent and that said Letters Patent is hereby corrected as shown below:

cancel claims 63, 64 and 65, renumbered 59, 60 and 61.

Column 22, line 47, delete "heteroaryl", and "heteroaryl-carbonyl"

Column 22, line 64 delete "heteroaryl" and "heteroaryl-carbonyl"

Signed and Sealed this

Twenty-fifth Day of August, 1992

Attest:

DOUGLAS B. COMER

*Attesting Officer*    *Acting Commissioner of Patents and Trademarks*